United States Patent [19]
Burkett

[11] Patent Number: 6,086,852
[45] Date of Patent: Jul. 11, 2000

[54] IN VIVO STAIN COMPOSITION, PROCESS OF MANUFACTURE, AND METHODS OF USE TO IDENTIFY DYSPLASTIC TISSUE

[75] Inventor: Douglas D. Burkett, Phoenix, Ariz.

[73] Assignee: Zila, Inc., Phoenix, Ariz.

[21] Appl. No.: 09/308,760

[22] PCT Filed: Nov. 13, 1997

[86] PCT No.: PCT/US97/20981

§ 371 Date: May 20, 1999

§ 102(e) Date: May 20, 1999

[87] PCT Pub. No.: WO99/25388

PCT Pub. Date: May 27, 1999

[51] Int. Cl.[7] .......................... A61K 49/00; G01N 31/00; G01N 33/48
[52] U.S. Cl. ........................... 424/9.7; 424/1.11; 424/9.1; 544/35
[58] Field of Search ..................................... 424/1.11, 9.1, 424/9.3, 9.4, 9.6, 9.7; 546/1; 544/1, 3, 35, 37

[56] References Cited

U.S. PATENT DOCUMENTS

| | | | |
|---|---|---|---|
| 4,321,251 | 3/1982 | Mashberg | 424/1.11 |
| 5,372,801 | 12/1994 | Malmros et al. | 424/1.11 |
| 5,882,627 | 3/1999 | Pomerantz | 424/9.7 |

OTHER PUBLICATIONS

McKamey et al, J. of Pharmaceutical Sciences, vol. 64, No. 9, pp. 1456–1462, "Chromatographic Mass Spectral and Visible Light Absorption Characteristics of Toulidene Blue O & Related Dyes," Sep. 1975.

*Primary Examiner*—Jose' G. Dees
*Assistant Examiner*—Dameron Jones
*Attorney, Agent, or Firm*—Drummond & Duckworth

[57] ABSTRACT

N-demethylated and N,N-demethylated derivatives of toluidine blue O and compositions which include these derivatives and the conformational isomers of toluidine blue O. Improved methods for the detection of dysplastic oral tissue using such compositions.

Processes for synthesis of toluidine blue O products, in which a complexing agent is introduced prior to the last stage of oxidation of a three-step synthesis from N,N-dimethyl-ρ-phenylenediamine.

An HPLC method for characterizing toluidine blue O products in which the mobile phase is an aqueous solution of an organic acid.

10 Claims, 3 Drawing Sheets

IN VIVO STAIN COMPOSITION, PROCESS OF MANUFACTURE, AND METHODS OF USE TO IDENTIFY DYSPLASTIC TISSUE

This invention relates to novel biological stain compositions that are adapted for human in vivo topical application.

In particular the invention contemplates novel Toluidine Blue O ("TBO") dye products, products which contain TBO and specific TBO derivatives, in specific proportions.

According to another aspect, the invention pertains to new methods of manufacturing TBO compositions, including these novel TBO products.

In yet another aspect, the invention concerns in vivo methods of using such novel TBO compositions to identify suspect dysplastic, i.e., abnormal, tissue.

In still another and further aspect, the invention pertains to compositions, in vivo diagnostic methods of use thereof and processes for manufacture thereof, which are specially adapted for detecting suspect dysplastic oral tissue, especially cancerous and precancerous tissue.

The various embodiments of the invention and the practice thereof will be apparent to those skilled in the art, from the following detailed description thereof, taken in conjunction with the claims and in conjunction with the drawings, in which:

BACKGROUND OF THE INVENTION

Most oral lesions result from trauma. However, other oral lesions are dysplastic tumors, some of which may be benign, but some of which may be either cancerous or precancerous. In addition, many dysplastic lesions are small and easily missed on routine visual examination by dental clinicians.

An in vivo diagnostic test is known which identifies and delineates suspect dysplastic oral tissue. This screening test is generally described in the U.S. Pat. No. 4,321,251 to Mashberg and in the U.S. Pat. No. 5,372,801 to Tucci et al. More recently kits have been developed which make it possible for clinicians to quickly and easily administer the test, as part of other routine dental procedures, and thus identify and/or delineate suspect sites at a time when the patients are symptomless or while the dysplastic lesions are so small that they might be missed during normal visual examination. Once a suspect dysplastic lesion is identified by the Mashberg protocol, a regular biopsy sample can be taken and subjected to histological examination, to determine whether the lesion is malignant or precancerous. Kits for performing this test, containing premixed dye and rinse solutions in the proper quantities and concentrations, are licensed by Zila, Inc. and are available commercially in Canada from Germiphene, Inc. under the trademark ORASCAN™ and in The United Kingdom and Australia from Stafford-Miller Ltd. under the trademark "ORASCREEN®".

THE PRIOR ART

It has now been discovered that the organic dye content of the prior art TBO products which were typically commercially available, depending on the vendor, was relatively low. Typically, the combined areas of the 254 nm HPLC peaks (see HPLC procedure of Example 3), which represent the conformational isomers of TBO in these prior art products was only about ≅2%–75% of the combined areas of the 254 nm HPLC peaks which represent all of the TBO and TBO-related components, i.e., the two conformational isomers of TBO plus up to six TBO-related components.

Referring to FIG. 1, HPLC peaks 7 and 8 represent the two conformational isomers of TBO (shown here as the chloride salt):

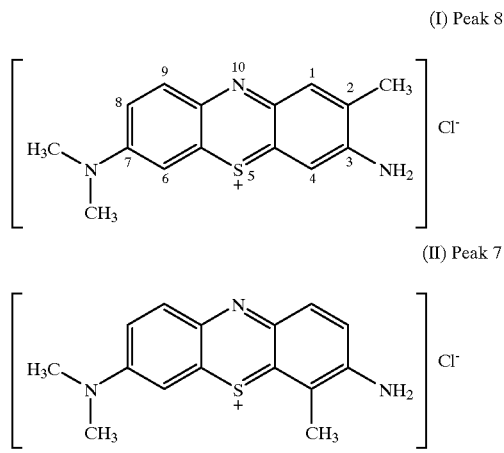

HPLC peaks 5 and 6 have been identified as the N-demethylated derivatives of the two conformational isomers of TBO:

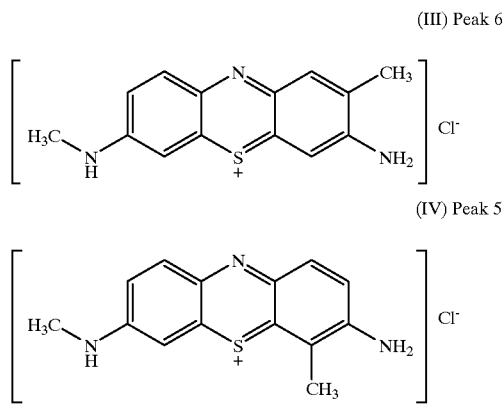

HPLC peaks 2 and 3 have been identifed as the N,N-demethylated derivatives of the two conformational isomers of TBO:

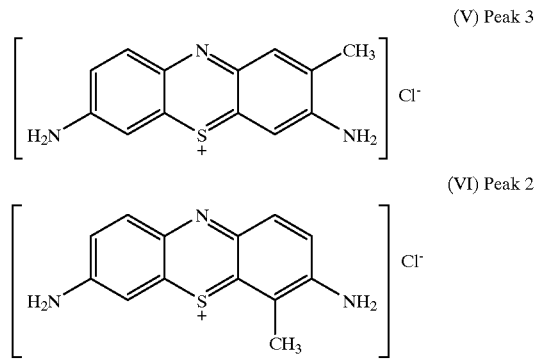

The exact structures of the compounds represented by HPLC peaks 1 and 4 have not been positively determined.

At any rate, in the TBO compositions of the prior art, a typical one of which is represented in FIG. 1, the compounds represented by peaks 1–4 were present in relatively higher amounts than those of the present invention (See FIG. 2) and the compounds represented by peaks 5–8 were present in relatively lower amounts than in the TBO products of the present invention. The two N-demethylated derivatives of the conformational isomers of TBO, represented by peaks 5 and 6, of the prior art (FIG. 1) were present in the relatively higher amounts, typically upwards of 20% of the organic dye content, than those which are present in the TBO products of my invention.

The classic synthesis of TBO is exemplified in the U.S. Pat. No. 418,055, issued Nov. 30, 1989, to Dandliker et al. This synthesis is a series of three oxidation steps: (1) oxidation of N,N-dimethyl-p-phenylenediamine, e.g., with potassium dichromate, to form 2-amino-5-dimethylaminophenyl thiosulfonic acid; (2) condensation of the thiosulfonic acid with o-toluidine, to form the corresponding indamine-thiosulfonic acid; and (3) ring closure of the indamine-thiosulfonic acid, e.g., in the presence of zinc chloride at boiling temperature for about 30 minutes, to form TBO. The reaction mixture is then cooled and the TBO product of the ring-closure reaction is complexed and salted out, e.g., by treatment with sodium chloride and zinc chloride, to precipitate the TBO complex, e.g., as an TBO/$ZnCl_2$ complex. Purification may be accomplished by repeated re-solution and re-precipitation, e.g., by re-solution in hot aqueous zinc chloride solution and re-precipitation with sodium chloride/zinc chloride.

As far as known, prior workers, who instigated the use of TBO for in vivo identification of dysplasia, used the above-described prior art TBO products, i.e., compositions in which the conformational isomers of TBO plus the N-demethylation and N,N-demethylation derivatives were less than 80% of the dye composition and in which the two N-demethylation derivatives of the conformational isomers, formed greater than about 20% % of the dye composition. According to my information, prior workers were unaware of the exact composition of their "TBO" products and manufacturers of prior art TBO products were unable to reproducibly prepare them. In fact, the prevalent literature description of the quality of TBO is "toluidine blue of good color value". The Biological Stain Commission specifies an analytical titration procedure for determining only the "organic dye content" of the material. The prior art use of such loosely defined "TBO" resulted in anomalous clinical observations and serious problems in obtaining necessary regulatory clearances to manufacture and market such products for use in human diagnostic procedures.

BRIEF DESCRIPTION OF THE INVENTION

Briefly, the new compositions of matter embodying the invention are a TBO product, in which the conformational isomers of TBO and the N-demethylation derivatives of these conformational isomers comprise and are present in a ratio of the TBO isomers to their N-demethylation derivatives such that the ratio of the combined areas of the 254 nm HPLC peaks representing the TBO isomers (determined in accordance with the HPLC procedure of Example 3) to the combined areas of the peaks representing their N-demethylation derivatives is at least about 6:1. Thus, as depicted in FIG. 2, the combined area of the 254 nm HPLC peaks, representing the TBO conformational isomers (peaks 7 and 8), is at least about six times the combined area of the 254 nm HPLC peaks, representing their respective N-demethylation derivatives (peaks 5 and 6). In the preferred embodiment of the invention, the components represented by peaks 5, 6, 7 and 8 equals at least about 95% of the organic dye content of the product. In the most particularly preferred embodiment, the peak 8 (254 nm) area represents at least 58% of the organic dye content of the product.

The invention also contemplates a method for human in vivo detection of dysplastic tissue, which includes the step of applying to human tissue the above-described new TBO products.

Still another embodiment of the invention is a process for reproducibly manufacturing TBO compositions, including the above-described novel TBO products, in which the complexing agent is added to the reaction mixture before the ring closure (third) step of the Dandliker synthesis, preferably before the first oxidation step (11, of FIG. 3) of the process.

The prior art Dandliker process included the steps of oxidizing N,N-dimethyl-p-phenylene diamine ions in a first reaction mixture to form a first intermediate, 2-amino-5-dimethylaminophenyl thiosulfonic acid, oxidizing the first intermediate and condensation of the oxidizate with o-toluidine, in a second reaction mixture, to form a second intermediate, indamine thiosulfonic acid, oxidizing the second intermediate in a third reaction mixture to close the indamine ring, forming a TBO reaction product, dissolved in the third reaction mixture, introducing a complexing reagent into said third reaction mixture, to form a TBO-complex product, and separating said TBO-complex from said third reaction mixture.

My improvement on this prior art Dandliker process comprises the step of adding the complexing reagent at a stage earlier than the formation of the third reaction mixture, preferably before the formation of the second reaction mixture.

According to a still further and presently preferred embodiment, specially adapted to manufacture the novel TBO product compositions of the invention, the temperature of the reaction mixtures during the oxidation steps is maintained at not greater than about 10° centigrade.

In yet another further and presently preferred embodiment, specially adapted to improve the quality of the TBO product, the pH of the reaction mixture during the oxidation steps is maintained in the range of about 2.8–3.8 (preferably 3.3) in the first reaction mixture, about 3.1–4.1 (preferably 3.6) in the second reaction mixture and about 3.0 in the third reaction mixture.

DETAILED DESCRIPTION OF THE INVENTION

Figure 1:
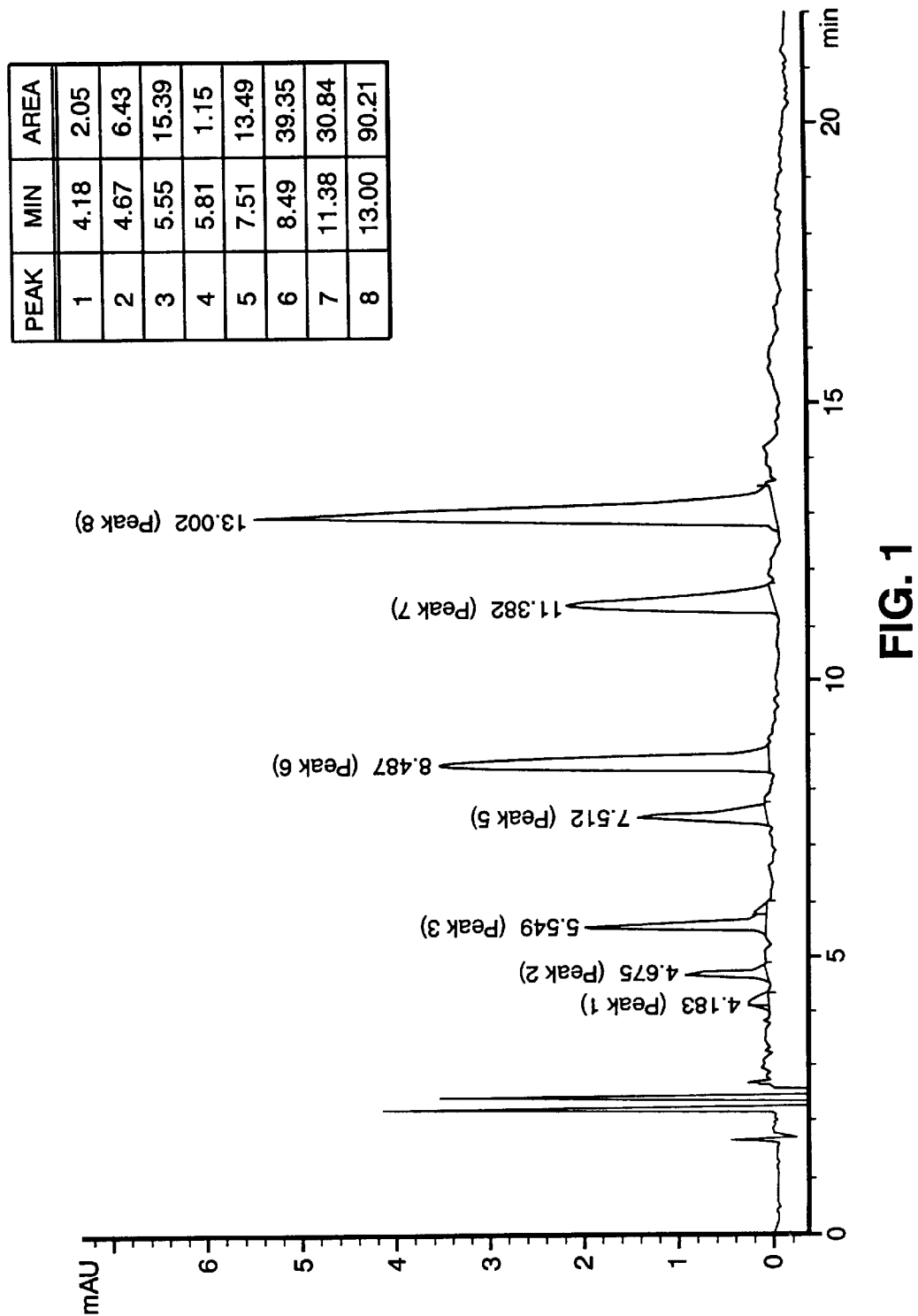
FIG. 1 is a 254 nm HPLC chart, depicting the peaks which are typically characteristic of TBO product compositions which were previously known and commercially available.

As depicted in FIG. 1, typical previously commercially available TBO exhibited two 254 nm HPLC peaks (peaks 7 and 8), which represent the conformational isomers of TBO, and two 254 nm HPLC peaks (peaks 5 and 6), which have been discovered by me to be the demethylation derivatives of the conformational isomers. The relative quantities of the conformational isomers of TBO to their N-demethylated derivatives in this typical prior art product was such that the peak area ratio of the conformational isomers to the N-demethylated derivatives is less than 4:1. A higher ratio, approaching or exceeding 6:1, accidentally existed in isolated prior art TBO products, but the relative amounts of such products were not known or considered important. In any event, TBO products with such higher ratios, could not be reproducibly prepared by prior art manufacturing procedures.

According to regulatory requirements based on recent clinical testing, TBO which is to be used in human diagnostic procedures (in general accordance with the Mashberg protocol) for detecting dysplastic tissue, must have an HPLC peak area ratio at 254 nm ratio of the conformational TBO isomers to the N-demethylation derivatives of at least about 6:1, i.e., the area of the combined 254 nm HPLC peaks 7 and 8, must be at least about six times greater than the area of combined 254 nm HPLC peaks 5 and 6.

It would be highly desirable to provide TBO product compositions which meet the requirements for human diagnostic testing procedures, in which the ratio of areas of the 254 nm HPLC peaks of the conformational isomers to the areas of their demethylation derivatives is at least 6:1. Further, it would be highly desirable to provide manufacturing processes for reliably and reproducibly preparing such TBO products, having this specific ratio of TBO isomers to TBO demethylation derivatives, and for reliably and reproducibly producing other TBO products with increased yield and overall purity.

Figure 2:
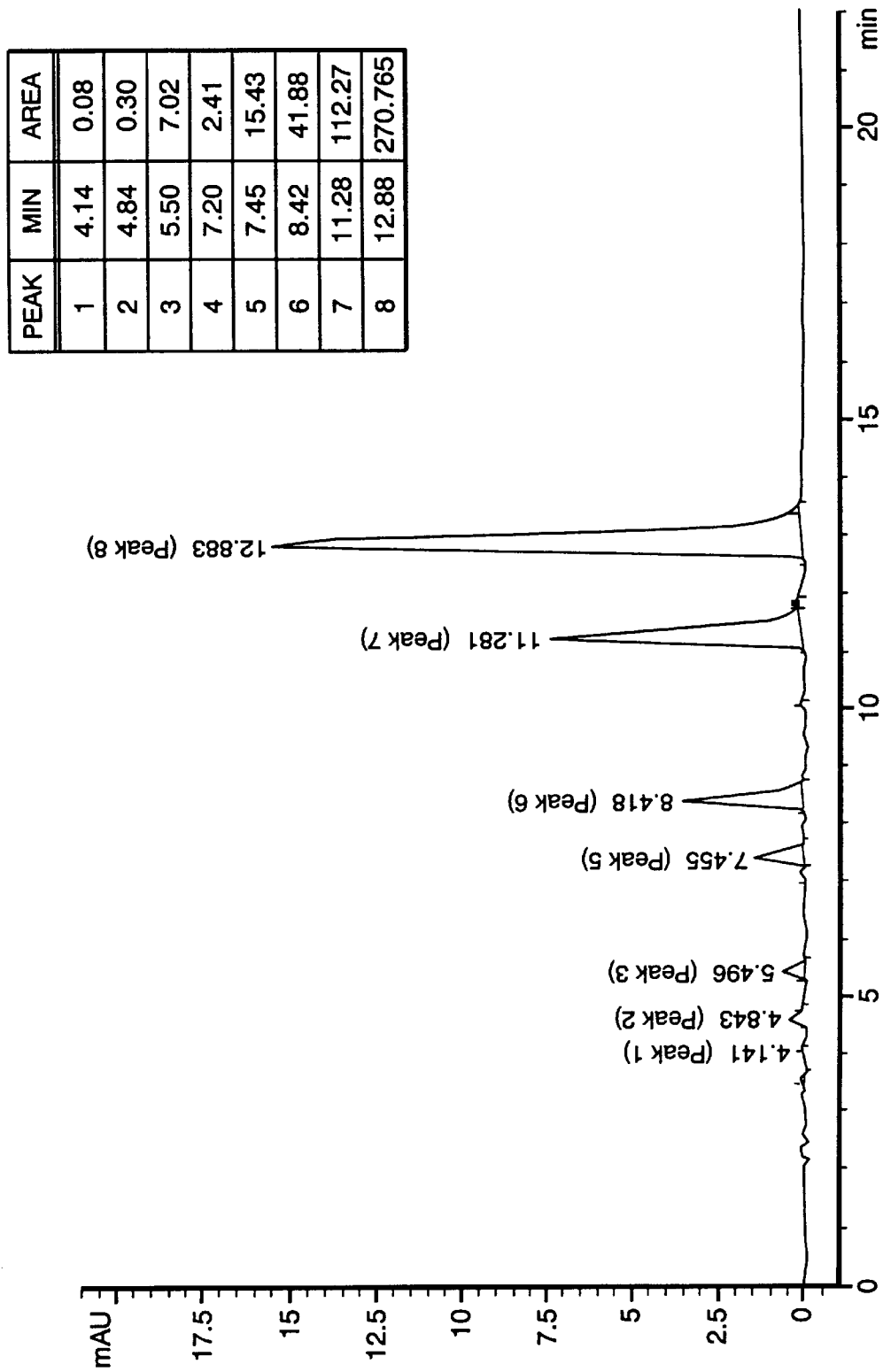
FIG. 2 is a 254 nm HPLC chart, depicting the peaks which are characteristic of typical TBO product compositions of the present invention.

As will be apparent from FIG. 2, which depicts a 254 nm HPLC analysis of typical compositions of the present invention, the peak area ratio of TBO conformational isomers to N-demethylation derivatives is greater than about 6:1, namely, 6.68:1, as demonstrated by the fact that the combined areas of 254 nm. HPLC peaks 7 and 8 is 6.68 times greater than the combined areas of peaks 5 and 6. The overall purity, determined by HPLC and ignition tests, and defined as [one hundred minus the percentage of ignition residue] multiplied by the HPLC purity (i.e., the sum of the areas of peaks 5, 6, 7 & 8 divided by the total peak areas) of the TBO products of the invention, is at least greater than 75%, compared to 2–10% for most of the prior art compositions. In isolated incidents, a comparable purity may have been obtained in prior art products, but not reproducibly.

According to one aspect of my invention, the ratio of the areas of the peaks (peaks 3, 6 & 8) with the ring methyl group in the 2-position (e.g., see Formula I) to the areas of the peaks (peaks 2, 5 & 7) with the ring methyl group in the 4-position (e.g., see Formula II) is ~2.5:1. By contrast, according to my knowledge, this ratio in the prior art products was no greater than 1.5:1.

This combination of high ratio of the areas of peaks 7+8: peaks 5+6 and the high ratio of the areas of peaks 3+6+8: peaks 2+5+7 has not to my knowledge been exhibited by any prior art product. Since peak 8 is the primary TBO peak, the structure of which is most widely accepted as TBO, then peaks 3, 6 and 8 are preferred to peaks 2, 5 and 7. Peaks 7 and 8 are, of course, preferred over peaks 5 and 6, which are, in turn, preferred over peaks 2 and 3. Thus, in the most preferred embodiment of my invention, the products satisfy the combination of these two ratio criteria.

Figure 3:
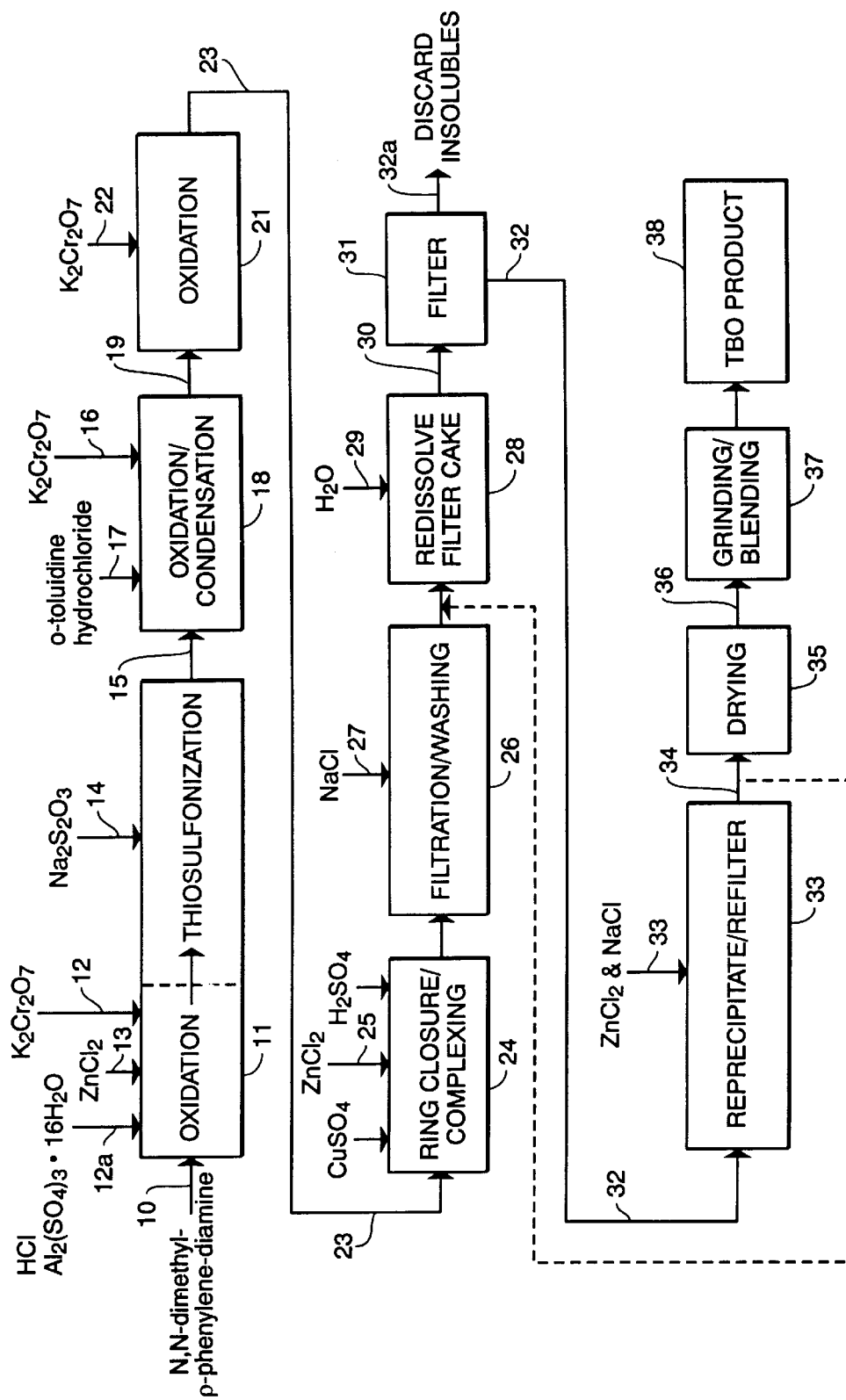
FIG. 3 is a process flow diagram, depicting the process which I have discovered, for manufacturing TBO products, including the novel TBO product compositions of the present invention.

FIG. 3 is a process flow diagram which depicts a process for preparing TBO products, which meet the regulatory requirements for clinical use in general accordance with the Mashberg protocol.

The starting material 10 for the synthesis of FIG. 3 is commercially-available, high-purity N,N-dimethyl,ρ-phenylene diamine:

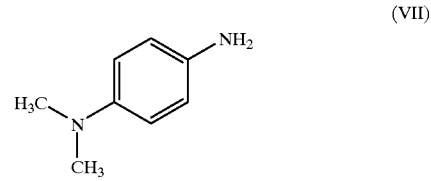

(VII)

Formation of First Reaction Mixture

An aqueous solution of the starting material 10 is oxidized 11, preferably at less than 10° C., especially at less than about 5° C., by reaction with a suitable oxidizing agent 12, e.g., potassium dichromate 12, in the presence of acid, aluminum sulfate and a reagent, 13 (which is believed to complex the intermediate(s) and is used in a later stage of the process to complex the TBO composition components), e.g., zinc chloride. Then, a source of thiosulfate ions 14, e.g., sodium thiosulfate, is added to form a first reaction mixture 15 containing the first intermediate, 2-Amino-5-dimethylaminophenyl thiosulfonic acid:

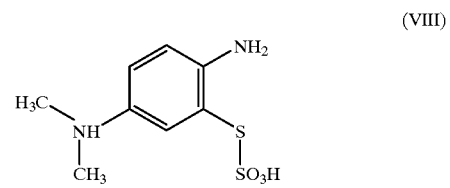

(VIII)

Formation of Second Reaction Mixture

The first reaction mixture 15 is then further reacted, preferably at a temperature of not greater than about 10° C., with additional oxidizing agent 16, e.g., potassium dichromate, and o-toluidine hydrochloride 17, in a condensation step 18 to form the second intermediate, a condensation product, indamine thiosulfonic acid

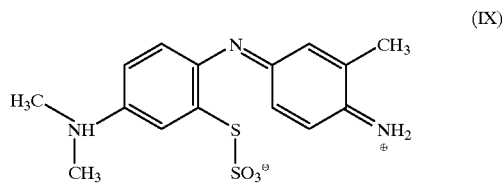

(IX)

in the second reaction mixture 19.

Formation of Third Reaction Mixture

The second reaction mixture 19 is then further oxidized 21, preferably by addition of a suitable oxidizing agent 22, e.g., potassium dichromate, at a temperature of not greater than about 10° C. This is followed by the addition of copper sulfate, zinc chloride complexing agent, acid and heating to 100° C. to effect closure of the indamine ring, forming TBO in a third reaction mixture 24. At this point the TBO is separated from the third reaction mixture and purified.

Separation/Purification of TBO

For example, in the presently preferred embodiment of the process of the present invention, the TBO is precipitated from the third reaction mixture by complexation of 24 with a suitable complexing agent 25, e.g., zinc chloride, to form the complex TBO-zinc chloride double salt. The precipitate is filtered 26 from the liquid phase and washed with sodium chloride solution 27. The washed filter cake is then redissolved 28 in a critical[1] volume of water 29 to form a TBO solution 30, which is then filtered 31 to remove undissolved solids 32a, which are discarded. Zinc Chloride, followed by a critical[2] volume/concentration of sodium chloride 33 is then added to the filtrate 32 to again precipitate the TBO-zinc

[1] If too much water is used it prevents isolation of the TBO. If too little water is used (1) all of the TBO does not get dissolved, reducing the yield and (2) it decreases the purity of the product.
[2] If too little sodium chloride is used, all of the product will not be salted out, reducing yield. If too much sodium chloride is used it will cause impurities to precipitate out along with the TBO, decreasing the purity of the product.

chloride double salt, illustratively (showing only one of the conformational isomers),

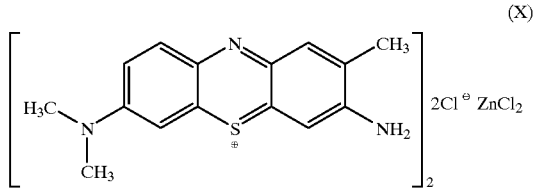

(X)

The TBO-zinc chloride double salt is separated from the mixture by filtration, to yield a TBO-zinc chloride/TBO hydrochloride filter cake 34.

As indicated by the dashed line 35, the TBO filter cake 34 can be redissolved, filtered, re-precipitated and reisolated multiple times to achieve the desired degree of purity and yield of TBO. The final purified filter cake complex product 34 is then dried 35, e.g., in conventional convection oven and/or vacuum oven and the dried filter cake 36 is ground and blended 37 to yield the final TBO product 38. The final TBO product contains both the zinc chloride double-salt of TBO (Formula X) and the chloride salt of TBO (Formulas I & II).

Introducing the complexing reagent before the formation of the third reaction mixture, i.e., prior to the oxidation of the indamine thiosulfonic acid and complexing the resultant TBO reaction product to form the TBO-complex, produces a TBO-complex product having an improved ratio of TBO conformational isomers to the N-demethylation products thereof. If the complexing reagent is introduced before the formation of the third reaction mixture, a ratio of at least 6:1 can be obtained. Of course, as will be recognized by those skilled in the art, obtaining these improved ratios of isomers to demethylation derivatives will also depend somewhat on observing other processing parameter precautions, as will be discussed below in connection with the disclosure of the preferred embodiments of the process invention, which are desirable to improve the yield and purity of the TBO-complex product. However, even if such other yield and purity-increasing precautions are observed, the desired improved ratios of isomers to N-demethylation products will not be obtained and the desired improved ratio of peaks with the methyl group in the −2 vs. −4 position will not be obtained, unless the complexing reagent is added at least before the formation of the third reaction mixture, i.e. before oxidizing the indamine sulfonic acid and complexing the resultant TBO product.

At present, I believe that the earlier addition of the complexing reagent, i.e., before the formation of the third reaction mixture improves the isomer:N-demethylation derivative ratio of the final product, because of the early formation of a complex of the starting material and/or the thiosulfonic acid and/or the indamine-thiosulfonic acid, which apparently offers steric hinderance to demethylation. In other words, the complex, because of its increased size and structure, offers steric bulk (and possibly electronic effects) which protect the N-methyl groups from oxidative demethylation. Because all three reaction steps involve oxidation and possible demethylation, the earliest formation possible of this complex is advantageous, which is why I recommend that the complexing agent be present as early as possible.

WORKING EXAMPLES

The following examples are presented to illustrate the practice of the invention in such terms as to enable those skilled in the art to make and use the novel TBO compositions, to practice the novel diagnostic methods using such TBO compositions and to practice the novel process for preparing TBO compositions, which together form the various embodiments of the invention, and to indicate to those skilled in the art the presently known best modes for practicing the various embodiments of the invention. These examples are presented as illustrative only and not as indicating limits on the scope of the invention, which is defined only by the appended claims.

Example 1

Manufacturing Process

This example illustrates, in the detail required to satisfy regulatory required GMP conditions, the exact procedures for carrying out the commercial scale manufacture of a batch of TBO dye product, according to the process which embodies the presently known best mode of the invention.

Preparation of Raw Materials Solutions

| Equipment/supplies: |
| --- |
| A. Ohaus IP15KS Balance |
| B. AnD HV150KAI Balance |
| C. Fairbanks H90-5150 Balance |
| D. OHAUS WB25/I-20W Balance |
| E. Cole Parmer (51201-30) and Thermolyne (S25535) Stirrers |
| F. Sampling devices, such as steel scoops, drum samplers, etc. |
| G. Erlyenmeyer flasks, beakers, carboys and other appropriate glassware. |
| H. Production Solution Labels. |

Safety:
Protective equipment, such as gloves, safety glasses, lab coats, and respirators should be worn when handling chemicals according to MSDS guidelines.

Raw Material Solutions Preparation Procedure:
To Hydrochloric Acid, 1364.2 g (±5.5 g) add 1364.2 g (±5.5 g) of USP Purified water. Stir until the solution is clear.

To Aluminum Sulfate Hexadecahydrate, 1779.1 g (±7.0 g) add 2548.9 g (±10.0 g) of USP Purified water. Stir until the solution is clear.

To Zinc Chloride, 7384.6 g (±30.0 g), add 2786.7 g (±11.0 g) of USP Purified water. Stir until the solution is clear.

To Potassium Dichromate, 2101.9 g (±8.0 g), add 25203.8 g (±100 g) of USP Purified water. Stir until the solution is clear.

To Sodium Thiosulfate Pentahydrate, 1526.6 g (±6.0 g), add 2043.6 g (±8.0 g) of USP Purified water. Stir until the solution is clear.

To Copper Sulfate Pentahydrate, 509.7 g (±2.0 g), add 1613.1 g (±6.0 g) of USP Purified water. Stir until the solution is clear.

To Sulfuric Acid, 600.0 g (±2.0 g), add 600.0 g (±2.0 g) of USP Purified water. Stir until the solution is clear.

To Sodium Chloride, 70.4 kg (±250 g), add 234.4 kg (±850 g) of USP Purified water. Stir until the solution is clear.

Safety

Protective equipment, such as gloves, safety glasses, lab coats, and respirators should be worn when handling chemicals according to MSDS guidelines.

Synthesis

Synthesis Equipment and Supplies:
LFE Control Panel (3000)
20 gallon Jacketed Glass Lined Purification Tanks with lid (E71224)
Two 100 gallon Jacketed Glass Lined Purification Tank with lids (P1, PT-001)(P2, L-13621)
FTS Recirculating Cooler (RC96C032) and 500 gallon Cold Storage Tank (500 CST)
Three Caframo Mixers (BDC-1850) (R1, 18500961)(P1, 18501148) (P2, 18501173) with shaft and impeller
Lightning Mixer (L1U08) (201550)
Three Heat Exchangers (Gardner Machinery) (R1, 01960763) (P1, 01960764) (P2, 08950727)
Three 12 KW Jacket Fluid recirculators (Watlow, BLC726C3S 20)
Three Recirculation Pumps (Sta-Rite, JBHD-62S, C48J2EC15)
Masterflex Digital Peristaltic Pump (A94002806)
Masterflex Peristaltic Pump (L95003320)
Cole Parmer Peristaltic Pump (B96002074)
Neutsche Filtration unit (70–2038, 43421-1)
Two Buchner Filtration Units (Z11,624-6, Z10,441-8)
Siemens Vacuum Pump (F2BV2)
60 Gallon Glass Lined Collection Tank with lid (86854, E164–1186)
Air Compressor (DF412-2) (9502312538)
Flow Controller (3–5500) (69705069190)
Six Batch Controllers (3–5600) (#1,69705069191, #2, 69705069199, #3, 69705069194, #4, 69705058829, #5, 69705058805, #6, 69705069195)
Six Flow Sensors (#1, 69704295165, #2, 69704024995, #3, 69704024994, #4, 69704025027, #5, 69612178606, #6, 69703120990)
Four Diaphragm Pumps (M1)
Four Surge Suppressers (A301H) (#2, 15557, #3, 15561, #4, 15558, #5, 15559)
Four Air Regulators (CFR10)
Four Solenoid Valves (used with air regulators)
Four Low Flow Sensors (FS-500)
Three Solenoid Valves (EASM5V16W20)
Air Filter / Regulator (T1R)PTFE / F06R113AC
Filter media, Polypropylene (7211-1)
Filter media, Whatman Grade 52
PharMed tubing (–18, –82, –90)
pH Meter; Hanna 9321 (1303675) & Orion 620 (001911)
Spectrophotometer 20 (3MU7202070)
Fisher Scientific Vacuum Oven (9502-033)
VWR 1370 FM forced air oven (1370 FM)
Dust/Mist Respirator
Thomas Wiley Laboratory Mill (3375-E10)
Patterson-Kelley Blender (Blendmaster, C416578)
OHAUS TS4KD Balance
OHAUS IP15KS Balance
Mettler AG 104 Balance
AnD HV150KA1 Balance
Fairbanks H90–5150 Balance
OHAUS AS123 Printer
OHAUS AS142 Printer
AD-8121 Multifunction Printer
Citizen iDP 3540 Dot Matrix Printer
Hewlett Packard HPLC (1050)
Ultrasonic Cleaner (8892-DTH, QCC9601 005C)
Type K Thermocouple Temperature Recorder (KTx, 6292753, 6355146)
Erlenmeyer Flasks (8 L, 6 L, 4 L, 1 L)
Beakers (8 L, 6 L, 500 mL, 250 mL)
Carboys (4 L, 10 L, 50 L)
HDPE Drums (55 gallon, 100 gallon)
Volumetric Flasks (100 mL)
Plastic Funnel
Pastuer Pipettes & Bulbs and Volumetric Pipettes (10 mL, 5 mL) & Bulb
Bellows (25 mL, 50 mL)
Weigh Paper
Spatulas
Packaging Material (containers, lids, labels)
Raw Material Solutions SYNTHESIS: Step 1

Synthesis of 2-amino-5-dimethylaminophenyl thiosulfonic acid

Check the integrity of the USP water system. To the reactor add the weighed USP Grade Purified Water (28,000 g ±100.0 g) and stir at 190±10 RPM. Record the conductivity of the USP water at the time the water was dispensed.

Add N,N-dimethyl-1,4-phenylenediamine (5.128 mol, 720.0 g±3.0 g). The material should be added as a powder (no lumps). Stir 10 minutes (±5 minutes).

Add hydrochloric acid (6 N, 1136.9 g ±5.0 g). Stir 15 minutes (±5 minutes).

Ensure the pH meter is calibrated according to SOP #LM-007. Take a reaction mixture sample of approximately 10 mL using a plastic sampling device. Mark the sample lot #.IPS1a. Check the pH and record. The pH must be 2.8–3.8 @25° C.±5° C.

Add aluminum sulfate hexadecahydrate solution (4328.0 g ±21.0 g). Stir 10 minutes (±5 minutes) at 275±10 RPM.

Add zinc chloride solution (3641.5 g ±18.0 g). Cool to 4° C.±1° C.

Once the temperature (PV1) is 4° C.±1° C. add potassium dichromate solution (6532.4 g ±32.0 g) over a 20 minute period (±5 minutes). When addition is complete stir 20 minutes (±5 minutes) and then change the Set Point (SP1) to 25.0° C. from the Main Menu.

When the temperature has reached 20.0° C. ±3.0° C. add sodium thiosulfate pentahydrate solution (3570.2 g ±18.0 g). Stir the solution at 25° C. for 30 minutes (±5 minutes).

Change the Set Point to 60° C. When the temperature (PV1) reaches 60.0° C. ±3.0° C. allow the reaction mixture to stir 5 minutes (±3 minutes) and change the Set Point on the LFE controller to 10.0.

Once the temperature has reached 13.0° C. ±2.0° C. take a reaction mixture sample of approximately 10 mL using a plastic sampling device. Mark the sample lot #.IPS1b. Check the pH and record. The pH must be 3.1–4.1@25° C. ±5° C.

SYNTHESIS: Step 2

Synthesis of Indamine Thiosulfonic Acid

Weigh out o-toluidine (604.4 g ±2.5 g) and cool to 18° C. ±3° C. in an ice bath. Add hydrochloric acid (6 N, 1230.7 g ±5.0 g) to the o-toluidine slowly. Remove the o-toluidine hydrochloride from the ice bath and allow the solution to cool to 38° C. ±3° C. Add the solution to the reaction mixture and stir 5 minutes (±3 minutes).

Add potassium dichromate solution (6532.4 g ±32.0 g) over a 20 minute period (±5 minutes). When addition is complete stir 10 minutes (±5 minutes).

Change the controller Set Point (SP1) to 60.0. Once the reaction mixture temperature reaches 60.0° C. ±3° C. allow the mixture to stir 25 minutes (±5 minutes). A precipitate will form consisting of a green indamine.

Take a reaction mixture sample of approximately 10 mL using a pipette. Mark the sample lot #.IPS2. Record the solution color.

SYNTHESIS: Step 3

Synthesis of Toluidine Blue O and Toluidine Blue O Zinc Chloride Double Salt Set the LFE controller Set Point to 7.0. Once the reaction mixture temperature reaches 10.0° C. ±3° C. add potassium dichromate solution (6532.4 g ±32.0 g) over a 20 minute period (±5 minutes). When addition is complete stir 20 minutes.

Add potassium dichromate solution (5225.9 g ±26.0 g) over a 20 minute period (±5 minutes). When addition is complete stir 20 minutes (±5 minutes).

Take a reaction mixture sample of approximately 10 mL using a pipette. Mark the sample lot #.IPS3.

Add zinc chloride solution (3641.5 g ±18.0 g). Stir 20 minutes (±5 minutes) at 350 ±10 RPM.

Add copper sulfate pentahydrate (2122.8 g ±10.0 g). Stir 15 minutes (±5 minutes).

Take a reaction mixture sample of approximately 10 mL using a pipette. Mark the sample lot #.IPS4.

Change the controller Set Point (SP1) to 100.0. Once the reaction mixture temperature reaches 67.0° C. ±3° C. begin to add sulfuric acid solution to pH 2.9±0.3 by adding aliquots (500 mL, 250, 125 mL, etc.). Stir for 5 to 10 minutes after each addition and check pH.

Once the reaction mixture temperature reaches 100.0° C ±3° C. allow the mixture to stir 35 ±5 minutes.

Change the controller Set Point (SP1) to 35.0. Once the reaction mixture temperature reaches 70.0° C. ±3° C. take a reaction mixture sample of approximately 10 mL using a pipette. Mark the sample lot #.IPS5.

Change the controller Set Point (SP1) to 2.5. Cool to 2.5° C. in 4 hours and Hold at 2.5° C. ±2.0° C. for 4 to 18 hours.

Take a reaction mixture sample of approximately 10 mL using a pipette. Mark the sample lot #.IPS6. Record the solution color. Check the pH and record. Filter the sample through 0.45 micron filter paper. Take approximately 100 milligrams of the precipitate and dissolve in approximately 100 mL of HPLC water. Filter the solution through 0.45 micron filter paper. Label the solution Lot #.IPS7 and analyze the sample by the RP-HPLC Toluidine Blue O Analysis Method. See Example 3. Record the results.

Purification: Step 1

Filter the reaction mixture through suitable filter media (Whatman Grade 52).

When the reactor is empty weigh out 24.0 kg ±150.0 g of 30% NaCl solution and add 24.0 kg ±150.0 g of USP water (record conductivity of the dispensed water). Close the reactor bottom valve and add the 15% NaCl solution to the reactor. Stir the solution briefly. When the filtration is complete add the NaCl solution to the filtration unit to rinse the filter cake. Collect the filtrate into the same container and Label lot#.HW1 (hazardous waste 1).

Process filtrate (lot#. HW1) according to waste disposal procedures.

Check the 100 gallon glass lined, jacketed purification tank #1 condition and make certain the tank has been properly labeled as CLEANED with date and signature. Equip the tank with a HDPE lid, Caframo stirrer, stir shaft, propeller and thermocouple probe inserted into a plastic thermocouple well. Check that the bottom valve is off and the outlet is capped.

Label the Tank with Lot#.P1A (Purification 1A).

Weigh out 190.0 kg ±1.0 kg of USP water into a HDPE container (record conductivity of the dispensed water) and transfer the water to Purification Tank 1. Stir the mixture at 350 RPM. Once the NaCl wash of the filter cake is complete add the filter cake to Purification Tank 1 while stirring.

Stir the mixture 2 to 4 hours. Take a sample (through the bottom valve) of approximately 50 mL. Mark the sample lot#.IPS8. Record the solution color.

Set the Purification Tank 1 LFE controller to 75.0 (SP1).

When the mixture temperature (PV1) reaches 75.0° C. ±3° C. change the Set Point on the controller to 40.0.

Allow the mixture to stir at 40° C. and 350 RPM for 12 to 36 hours.

Take a sample (through the bottom valve) of approximately 50 mL. Mark the sample lot#.IPS9. Record the solution color. Check the pH and record. Measure 1.0 mL of the sample with a 1.0 mL pipette and dilute to 100 mL in a volumetric 100 mL flask. Label the sample lot#.IPS9A. Then take 10.0 mL of this solution with a 10.0 mL pipette and dilute to 100 mL in a volumetric 100 mL flask. Label the sample lot#.IPS9B. Measure the absorbance of these samples using the spectronic 20+. Record the results. The absorbance of sample 9B should be $\geq 0.220$.

Purification: Step 2

Filter the mixture through filter media in the filtration unit. Collect the filtrate into a Tared HDPE container with lid.

Check the 100 gallon glass lined, jacketed purification tank # 2 condition and make certain the tank has been properly labeled as CLEANED with date and signature. Equip the tank with a HDPE lid, Caframo stirrer, stir shaft, propeller and thermocouple probe inserted into a plastic thermocouple well. Check that the bottom valve is labeled as CLEANED, off (horizontal position) and the outlet is capped.

Label the Tank with Lot#.P2A (Purification 2A), date and signature.

When the filtration is complete weigh the container and solution. Subtract the tare weight. Record the solution weight. Calculate the solution volume.

(TBO soln wt. g)(100.0 mL TBO soln/100.42 g TBO soln) =ml of TBO soln

Label the filter cake lot#.HW2 (Hazardous Waste 2) and process according to waste disposal procedures.

Into a clean HDPE container weigh out a quantity of 30% NaCl solution equal to the solution volume recorded above using the following formula:

(mL of TBO soln) (116.91 g NaCl soln/100.0 mL NaCl soln)=g of NaCl soln

Sample ≈10 mL of the filtrate and check the pH. Label lot#.IPS10. The pH must be 3.0–4.0. Transfer the filtrate (by weight) to Purification Tank 2. Stir the solution at 350 RPM.

Add zinc chloride solution (1636.3 g ±6.5 g)

Transfer the NaCl solution (by weight) to Purification Tank 2.

Set the Purification Tank 2 LFE controller to 75.0 (SP1).

When the mixture temperature (PV1) reaches 75.0° C. ±3° C. change the Set Point on the controller to 5.0.

Cool to 5° C. in 6 hours and Hold at 5° C. ±4.0° C. for 4 to 24 hours.

Take a sample (through the bottom valve) of approximately 50 mL. Mark the sample lot#.IPS11.PT2.

PROCESSING i. Filter

Filter the mixture through tared filtration media (Whatman Grade 52) in the filtration unit Weigh out 12 kg ±50 g of 30% sodium chloride solution and dilute with 12 kg ±50 g of USP water (record conductivity of the dispensed water). Wash the filter cake with the 15% sodium chloride solution by adding the solution directly to the buchner. When the filtration is complete carefully remove the filter paper containing the toluidine blue O product.

Process Lot#.HW3 (Hazardous Waste 3) according to waste disposal procedures.

ii. Dry

Place the TBO product in the oven and dry at 50.0° C. ±3.0° C. for 5 ±1 hours. Label the oven lot#.PRE-DRY.

Remove the product from the forced air oven and place in the Vacuum Oven. Dry at 45.0° C. ±3.0° C. @ 28" Hg ±2" Hg for 10 ±2 hours. Label the oven lot#.DRY.

iii. Weigh

Remove the product and weigh the Toluidine Blue O and filter. Subtract the filter weight and record the TBO weight.

Using a stainless steel spatula carefully remove the product from the filter paper. Wear a Dust/Mist respirator. Weigh the Toluidine Blue.

iv. Grind

Transfer the product to the TOLUIDINE BLUE O FINISHING AREA. Check the Thomas Wiley Laboratory Mill condition and make certain the mill has been properly labeled as CLEANED with date and signature. Use the 0.5 mm screen. Attach a clean container to the delivery chute. The chamber door must be closed and latched.

Close the sliding shutter at the bottom of the hopper, remove the hopper lid and add the sample. Replace the hopper lid. Turn the mill ON and open the sliding shutter slightly. Feed sample into the mill chamber slowly enough so that the mill does not slow down or become jammed.

Once the grinding is complete carefully remove the mason jar from the delivery chute.

v. Blend

Check the Patterson-Kelly Lab Blender condition and make certain the blender has been properly labeled as CLEANED with date and signature.

Transfer the Toluidine Blue O product to the blender container and close the lid. Set the timer to 15 minutes ±5 min.

vi. Test

Sample the product for testing. Analyze the sample by the RP-HPLC Toluidine Blue O Analysis Method. Record the results.

Example 2

Clinical Testing Protocol

Preparation of Clinical Test Solutions

This example illustrates the use of the TBO product of Example 1A in the identification of oral dysplasia.

The TBO product of Example 1, raspberry flavoring agent (IFF Raspberry IC563457), sodium acetate trihydrate buffering agent and $H_2O_2$ (30% USP) preservative (See U.S. Pat. No. 5,372,801), are dissolved in purified water (USP), glacial acetic acid and SD 18 ethyl alcohol, to produce a TBO test solution, having the composition indicated in Table A:

TABLE A

| Component | Weight % |
|---|---|
| TBO Product | 1.00 |
| Flavor | .20 |
| Buffering Agent | 2.45 |
| Preservative | .41 |
| Acetic Acid | 4.61 |
| Ethyl Alcohol | 7.48 |
| Water | 83.85 |
| | 100.00 |

Pre-rinse and post-rinse test solutions of 1 wt. % acetic acid in purified water, sodium benzoate preservative and raspberry flavor are prepared.

Clinical Protocol

The patient is draped with a bib to protect clothing. Expectoration is expected, so the patient is provided with a 10-oz. cup, which can be disposed of in an infectious waste container or the contents of which can be poured directly into the center of a sink drain, to avoid staining the sink. Environmental surfaces or objects which might be stained are draped or removed from the test area.

A visual oral cancer examination is conducted, without using any instruments which might cause nicks or cuts of soft tissues. Notations are made of the pre-staining appearance of soft tissues and teeth.

The patient rinses the oral cavity with approximately 15 ml. of the pre-rinse solution for approximately 20 seconds and expectorates, to remove excess saliva and provide a consistent oral environment. This step is then repeated with additional pre-rinse solution.

The patient then rinses and gargles with water for 20 seconds and expectorates.

The patient then rinses and gargles with 30 ml. of the TBO test solution for one minute and expectorates.

The patient then rinses with 15 ml. of the post-rinse solution for 20 seconds and expectorates. This step is then repeated.

The patient then rinses and gargles with water for 20 seconds and expectorates. This step is then repeated.

Observations of the oral cavity are then made, using appropriate soft-tissue examination techniques, including retraction, well-balanced lighting and magnification, if necessary. The location, size, morphology, color and surface characteristics of suspect lesions, that have retained blue coloration are made and recorded.

In order to reduce false positives, the patient is brought back after 10–14 days for a repeat of the above protocol. This period allows time for healing of any ulcerative or traumatic lesion or irritating etiology at the time of the first examination. A positive stain after the second examination of a suspect area detected in the first examination is considered an indication of cancerous or precancerous tissue and a biopsy is made to confirm this conclusion.

Early erythroplastic lesions stain blue, often in a stippled or patchy pattern. However, it normal for the stain to be retained by the irregular papiliar crevices on the dorsum of the tongue, which is not a positive indication. Other areas which retain blue stain, but are not regarded as positive include dental plaque, gingival margins of each tooth, diffuse stain of the soft palate because of dye transferred from the retained stain on the dorsum of the tongue, and ulcerative lesions which are easily distinguished. In all instances, where a lesion is highly suspect, but does not stain positively with this test, it is nevertheless imperative that a biopsy be taken.

Example 3

HPLC Procedure

This example describes a procedure for analysis of TBO samples, for use in identifying, assaying and purity testing.

| Equipment and Supplies |
| --- |
| Acetonitrile, HPLC Grade |
| Glacial Acetic Acid, reagent grade |
| Ammonium Acetate, reagent grade |
| Deionized Water, suitable for HPLC analysis |
| pH Meter, with standard pH 4.0 and 7.0 buffers |
| Laboratory glassware, including volumetric flasks and pipettes |
| Ultrasonic Bath |
| Analytical Balance |
| Magnetic Stirrer |
| Compressed Helium |
| Filtration Apparatus with 0.45 micron nylon filters |
| 100 µL Syringe |

HPCL Chromatograph and Accessories, including

Hewlett Packard Series 1050 pump, or equivalent capable of isocratic high-pressure flow Hewlett Packard Series 1050 Diode Array Detector, or equivalent wavelength UV detector Hewlett Packard Vectra Series 3 Disk Drive (computer controller) with Ultra VGA 1280 Monitor and laser printer, or equvalent integrating recorder Prodigy, 5 µ, QDS (3) 100Å, 2.5 cm×4.6 mm, or equivalent HPLC column Fixed-loop injector (10 or 20 AL)

Column Heater

Preparation of the Mobile Phase

Prepare one liter of 0.01 M ammonium acetate solution by transferring 0.77 g of ammonium acetate to a 1000 mL volumetric flask. Add water, mix to dissolve and dilute to mark with water. Transfer the 0.010 M ammonium acetate solution to an Earlenmeyer flask and stir with magnetic stirrer. Using pH meter previously calibrated with pH 4.0 and 7.0 buffers, adjust pH of solution to between 3.3 and 3.6 with acetic acid. Filter the solution through a 0.45 µfilter. Filter acetonitrile through 0.45 µ nylon filter, using Millipore filtration apparatus and add exactly 250 mL to the stirred aqueous ammonium acetate solution. Place this reservoir of the mobile phase in position for access by the HPLC pump and purge with helium for 5–10 minutes.

Preparation of TBO Samples

Accurately weigh about 50 mg of TBO sample, transfer to a 100 mL volumetric flask and dilute to the mark with water. Cap the flask, sonicate for 30 minutes and mix. This is a stock solution of about 0.5 mg/mL.

Transfer 10.0 mL of the stock solution to a 100 mL volumetric flask, dilute to the mark with water and mix. This approximately 0.05 mg/ml diluted TBO working solution is labeled appropriately.

Chromatographic Conditions

Injection volume—10 or 20 µL

Flow rate—about 1.5 mL/minute

Column Temperature—40° C.

Detector wavelength—254 nm

Sensitivity and attentuation settings: appropriate for instrument used

Integration—Area Response

HPLC Analysis of Samples

Set up and allow HPLC to equilibrate with the mobile phase flow. System suitability tests as per USP XXIII are used to verify the precision and accuracy of the HPLC data obtained. For each assay, evaluate the following parameters:

| Precision: | A minimum of five injections of the working sample are compared. The Relative Standard Deviation (RSD) must be equal to or less than 2.0%. Six injections are made if the RSD is greater than 2.0%, but less than 3.0% for the combined areas of peaks 5–8. |
| --- | --- |
| Resolution: | Calculate the baseline resolution of peaks 7 and 8 (the major peaks) on one chromatogram of the sample by the following equation: |
| | $$R = \frac{2(t_2 - t_1)}{w_1 + w_2}$$ |
| | where<br>$t_1$ = retention time, in mm, of peak 7<br>$t_2$ = retention time, in mm, of peak 8<br>$w_1$ = peak width, in mm, of peak 7<br>$w_2$ = peak width, in mm, of peak 8<br>The resolution between peaks 7 and 8 must be greater than 1.5. |
| Tailing: | Measure the peak symmetry to insure the quantitation of area under the peak is accurate. Calculate the tailing factor (T) for peaks 7 and 8 on one chromatogram of the sample; by the following equation:<br>$T = W_{0.05} \div 2f$<br>where<br>$W_{0.05}$ = width of peak determined at 5% from the baseline peak of the peak height<br>$f$ = distance between peak maximum and peak front at $W_{0.05}$ |
| T should be less than a factor of 3. | |

Record the chromatograms and determine the area response of the main peaks (5, 6, 7 and 8), as well as all impurity peaks which are detected (all peaks other than solvent front peaks) appearing in the chromatogram.

Calculations and Other HPLC Determinations

Identity (TBO drug substance and drug product):

The chromatographic profile of the sample preparation should show the same general profile (peak presence and peak intensities) as that of the chromatogram depicted in FIG. 2.

Related Substances (drug substance):

The quantity of each impurity peak (the known impurities designated as peaks 1, 2, 3 and 4 plus any other impurity peak) is calculated as an area percent versus the total area of all peaks in the chromatogram.

Assay of the TBO drug substance:

The percentage of each of the four main tbo peaks (peaks 5–8) is determined as for the impurities, i.e., $$\text{HPLC Purity} = \frac{\text{sum of peak areas 5–8}}{\text{sum of all peak areas}} \times 100$$

Having described my invention in such terms as to enable those skilled in the art to understand and practice it and, having identified the presently preferred best modes thereof, I claim:

1. A composition of matter, comprising:
   (A) the conformational isomers of toluidine blue O, the compounds having the structures

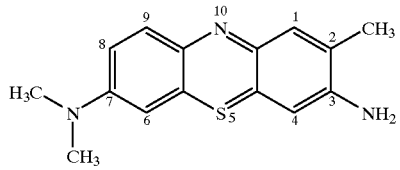

and

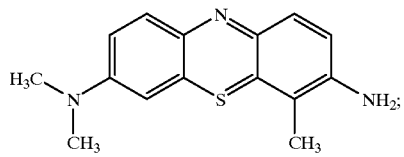

and (B) the N-demethylation derivative of said isomers, the compounds having the structures

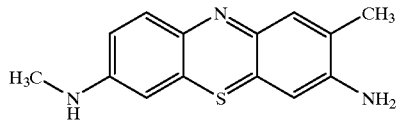

and

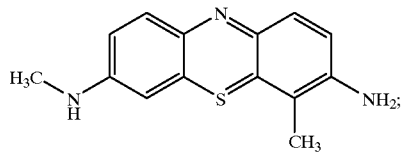

the ratio of the combined areas of the 254 nm HPLC peaks representing said isomers to the combined areas of the peaks representing said N-demethylation derivatives being at least about 6:1.

2. A composition of matter, comprising:

(A) a first group of components, comprising a conformational isomer of toluidine blue O having the ring methyl group in the −2 position, the compound having the structure

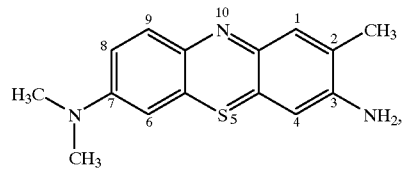

an N-demethylation derivative thereof, the compound having the structure

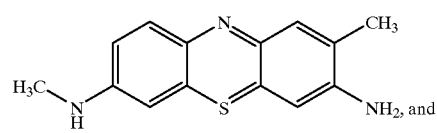

an N,N-demethylation derivative thereof, the compound having the structure

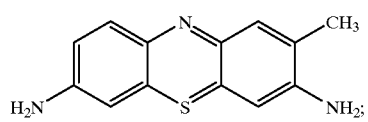

and (B) a second group of components, comprising a conformational isomer of toluidine blue O having the ring methyl group in the −4 position, the compound having the structure

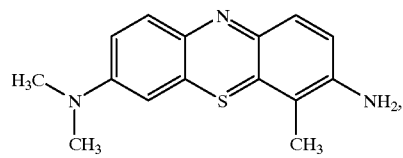

an N-demethylation derivative thereof, a compound having the structure

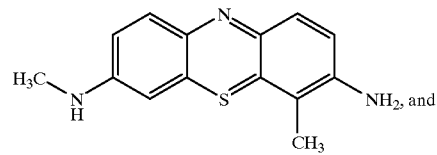

an N,N-demethylation derivative thereof, the compound having the structure

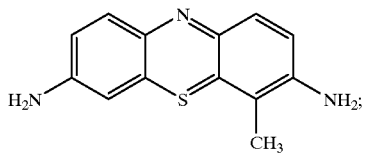

the ratio of the combined areas of the 254 nm HPLC peaks representing said first group to the combined areas of the 254 nm HPLC peaks representing said second group being at least about 2.5:1.

3. A composition of matter, comprising conformational isomers of toluidine blue O, namely the compounds having the structures (a)

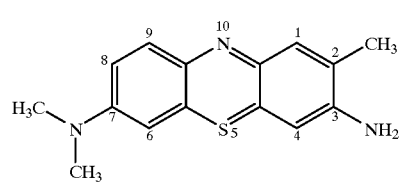

and (b)

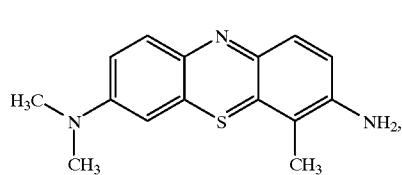

in which said isomer of subparagraph (a) comprises at least 58% of the total organic dye content of said composition.

4. In a method for identification of dysplastic tissue, which method includes applying a biological stain to human tissue which selectively stains dysplastic tissue, the improvement comprising the step of applying to human oral tissue the composition of claim 1 in a liquid carrier.

5. In a process for manufacturing toluidine blue O, which process comprises the steps of (A) oxidizing N,N-dimethyl-p-phenylene diamine in a first reaction mixture, to form a first intermediate, 2-amino-5-dimethylaminophenyl thiosulfonic acid, (B) oxidizing said first intermediate and condensing the oxidizate in a second reaction mixture with o-toluidine, forming a second intermediate, indamine thio-sulfonic acid, (C) oxidizing said second intermediate to close the indamine ring thereof, forming a TBO-containing reaction product dissolved in a third reaction mixture, (D) introducing a complexing reagent into said third reaction mixture, to form a TBO-complex product dissolved in said third reaction mixture, (E) precipitating said TBO-complex product from said third reaction mixture, and (F) separating said TBO-complex product, containing the conformational isomers of TBO, the compounds having the structures

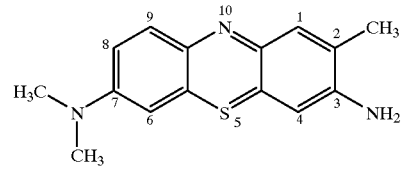

and

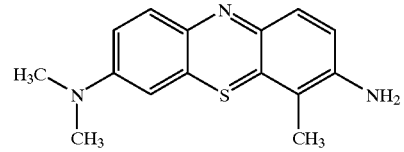

N-demethylation derivatives of said isomers, compounds having the structures

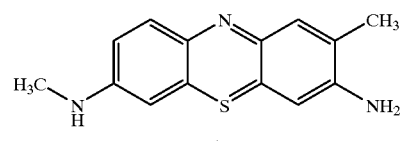

and

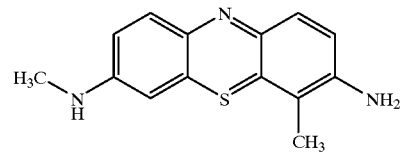

N,N-demethylation derivative of said isomers, compounds having the structures

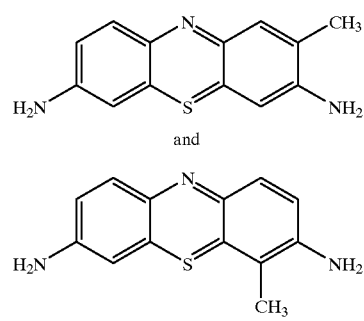

from said third reaction mixture, the improved process comprising introducing said complexing reagent to a reaction mixture before the formation of said third reaction mixture, said complexing reagent being a compound that forms with said N,N-dimethyl-p-phenylenediamine, said first intermediate, and/or said second intermediate, a complex that provides steric hinderance to demethylation thereof.

6. The process of claim 5 in which the temperature of the reaction mixtures during the oxidation steps is maintained at not higher than about 10° C.

7. The process of claim 5 in which the pH of the reaction mixtures is maintained in the range of about 2.8–3.8 in the first reaction mixture, about 3.1–4.1 in the second reaction mixture and about 3.0 in the third reaction mixture.

8. A compound which a member selected from the group consisting of N-demethylated derivatives of the conformational isomers of toluidine blue O, from the group consisting of the compounds having the structural formulas

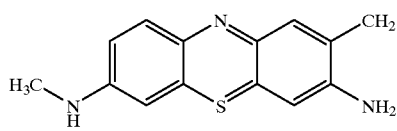

and

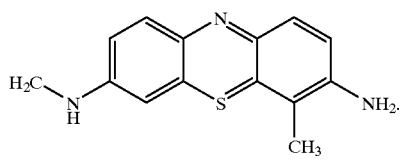

9. A compound which is a member selected from the group consisting of N,N-demethylated derivatives of the conformational isomers of toluidine blue O, from the group consisting of the compounds having the structural formulas

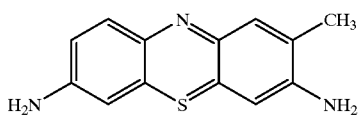

and

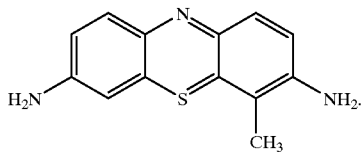

10. In an HPLC method for analysis of a toluidine blue O dye product, said method including forming a mobile phase, forming a TBO sample solution, equilibrating an HPLC column with the mobile phase flow, and injecting the sample solution into the HPLC column, the improvement for identifying sample dye components and for assaying and determining the purity of said sample, said improvement comprising forming said mobile phase as a composition comprising a water-soluble salt of an organic acid.

* * * * *